United States Patent [19]

Ryan et al.

[11] Patent Number: 5,076,699

[45] Date of Patent: Dec. 31, 1991

[54] METHOD AND APPARATUS FOR REMOTELY AND PORTABLY MEASURING A GAS OF INTEREST

[75] Inventors: Frederick M. Ryan, Loyalhana Twp., Westmoreland County; Milton S. Gottlieb, Churchill, both of Pa.

[73] Assignee: Rosemount Analytical Inc., LaHabra, Calif.

[21] Appl. No.: 345,858

[22] Filed: May 1, 1989

[51] Int. Cl.$^5$ .......................... G01N 21/59; G01B 9/02
[52] U.S. Cl. ..................................... 356/437; 356/352; 356/346; 250/338.1; 250/339
[58] Field of Search ............... 250/346, 354, 339, 351, 250/253, 343, 504 R, 493.1, 338.1, 338.5, 255; 356/352, 320, 309, 434, 437, 365; 372/18, 21, 32, 354; 370/1, 3

[56] References Cited

U.S. PATENT DOCUMENTS

| | | | |
|---|---|---|---|
| 3,171,027 | 2/1965 | Wallack . | |
| 3,370,503 | 2/1968 | Keahl . | |
| 3,939,348 | 2/1976 | Barrett | 250/339 |
| 4,035,643 | 7/1977 | Barrett | 250/339 |
| 4,204,771 | 5/1980 | Shull et al. | 356/346 |
| 4,221,472 | 9/1980 | Smith et al. | 356/352 |
| 4,496,839 | 1/1985 | Berstein et al. | 250/253 |
| 4,594,511 | 1/1986 | Cooper et al. | 250/351 X |
| 4,779,959 | 10/1988 | Saunders | 350/346 |
| 4,905,169 | 2/1990 | Buican et al. | 356/365 |

FOREIGN PATENT DOCUMENTS 0203767 12/1986 European Pat. Off. .
2274914 1/1976 France .
2174198 10/1986 United Kingdom .

OTHER PUBLICATIONS

Frölich et al., Tuning Properties of a Birefringent Fabry-Perot Etalon/Appl. Phys. 9, No. 3 (Mar. 76), pp. 205-207, copy 356/352.

Article entitled "Scanning the Field for Ideas", reprinted from *Machine Design*, vol. 54, No. 24 (Oct. 1982).

Primary Examiner—Vincent P. McGraw
Assistant Examiner—LaCharles P. Keesee
Attorney, Agent, or Firm—Kinney & Lange

[57] ABSTRACT

A remote gas measuring apparatus and method utilizes the optical absorption line characteristics to determine an amount of gas of interest as may exist in an area under study. The remote gas measuring apparatus includes a source of electromagnetic radiation that can be projected toward the area in question and a light collecting arrangement. The light signal received is coupled to a fast light switch modulator which modulates the light signal to a first frequency. A second modulating arrangement modulates the light signal to a second frequency and includes a birefringent etalon device having a periodic spacing equal to the periodicity of the absorption lines of the gas of interest. The second modulating means is further effective such that, when an electric field is applied thereto the transmission spectra associated with the light signal is shifted between spectra which coincide with the absorption lines and spectra which fall between the absorption lines. The light signal from the etalon device is then conditioned and input to a detector configuration which distinguishes between the light signal at the first frequency and the light signal at the second frequency in order to determine at least a quantity of the gas of interest.

15 Claims, 5 Drawing Sheets

FIG. 3a
GAS ABSORPTION
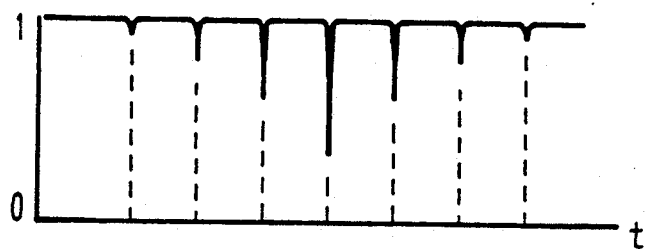
FIG. 3b
CORRELATION ETALON
FIG. 3c
ANTI CORRELATION
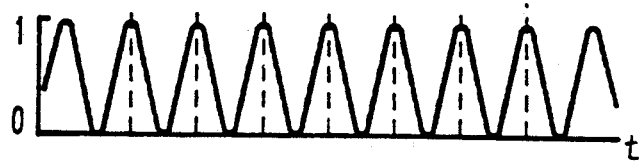
WAVELENGTH
FIG. 3d
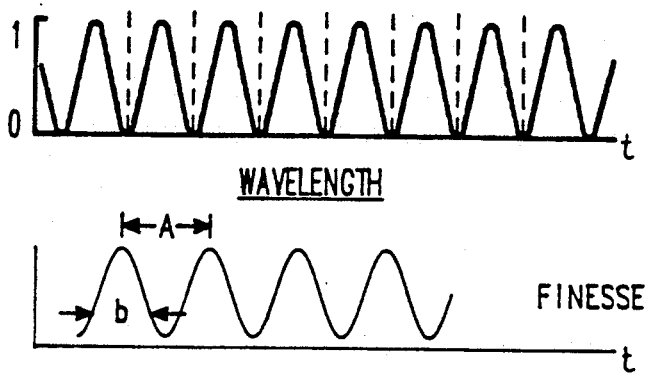
FINESSE = A/b
FIG. 3e
FINESSE = 2
FIG. 3f
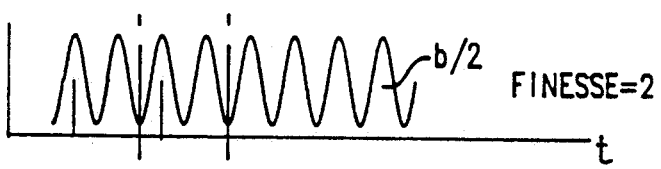
FINESSE = 4
FIG. 3g
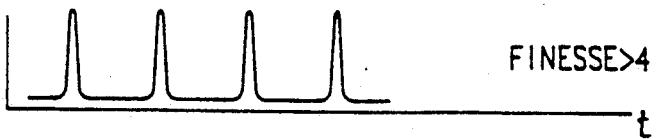
FINESSE > 4

METHOD AND APPARATUS FOR REMOTELY AND PORTABLY MEASURING A GAS OF INTEREST

CROSS-REFERENCE OF RELATED APPLICATION

The present invention is related to material disclosed in the following co-pending U.S. Patent which is assigned to the same assignee as the present application. U.S. Pat. No. 4,998,017, to be assigned, "An Improved Method and Arrangement for Measuring the Optical Absorptions of Gaseous Mixtures" filed May 1, 1989 by F. M. Ryan and M. S. Gottlieb.

FIELD OF THE INVENTION

This invention relates to a method and apparatus for measuring a gas of interest using a remote, portable instrument. More particularly, this invention relates to such a method and apparatus as utilizes interferometric techniques combined with light sampling techniques to measure the optical absorption of the gas of interest and to determine therefrom, the quantity of such gas as may be present.

BACKGROUND OF THE INVENTION

In the field of gas analyzing and measuring technologies, there has been an increased need for more accurate instruments and techniques that can be operated quickly and in a number of different, often difficult surroundings. One such situation where this need arises is in the field of mine safety where it is necessary to quickly and accurately monitor methane gas levels. In a mine environment, it can be appreciated that methane can occur in randomly distributed pockets that must be remotely detected and/or measured prior to human exposure to such gas. Additionally, since such detection or measurement must be accomplished in a confined area having dimensions which can vary infinitely, the instrument which accomplishes this detection or measurement must be portable and furthermore must be capable of operating over distances that can vary significantly.

Presently, for purposes of detecting the presence of methane in a mine environment, a hand held catalytic detector is typically used which must be taken up to the working face in order to detect the presence of methane. This is a dangerous and time consuming operation and it would be a great advantage if the detection operation could be performed at a distance away from the coal face.

There are other existing gas detection and/or measurement techniques that can effectively recognize methane, however, such techniques accomplish this task in a manner that does not lend itself to remote, portable instrument applications. For instance, if a solid electrolyte sensor were used, it would be necessary to provide a sample of methane gas as a reference to be introduced to the reference cell side of the sensor. U.S. Pat. No. 3,915,830 which issued to A. O. Isenberg on Oct. 28, 1975, discloses that when the gas environment under study is exposed to the sensing electrode of the cell, an EMF signal is generated which corresponds to the difference and partial pressure in the gas species across the electrolyte.

To utilize this technology in a mine environment or any other environment which would require quick, accurate measurements in a large number of randomly sized areas, would exceed the practical capabilities of this technology. It is known that such sensors are used in a probe type of device which must be placed in proximity to the gas of interest for a specific period of time in order to achieve a sufficient reading. Accordingly, an application which requires essentially a scanning operation over the area in question would be impractical for this technology.

Another technology which has proven promising in the area of gas analysis and measurement utilizes the measurements of the optical absorption properties of the particular gas to detect and or quantify such gas. This technique takes advantage of the fact that, at specific light wavelengths, certain gases exhibit specific absorption characteristics. An example of the use of spectrographic techniques for gas detection can be found in a device known as an acousto optic tunable filter, commonly known as an AOTF. U.S. Pat. No. 3,792,287 issued to G. W. Roland et al. on Feb. 12, 1975 discloses the use of a Thallium Arsenic Selenide (TAS) crystal which has the property that, with infrared light applied in one direction to the crystal and an RF signal applied in another direction to the crystal so as to intercept the infrared light signal, based on the geometry of the crystal, there is formed thereby, a specific absorption bandwidth by which the detection of the gas having absorption properties coinciding with this bandwidth can be detected and/or quantified. Although this approach has proven effective for a number of industrial environments such as in a combustion control process, it also does not lend itself to an application in an environment where it is necessary to scan areas of unknown size and composition to detect pockets of the gas of interest.

Still another technology used in the area of gas analysis and measurement is that of differential absorption spectroscopy where a dispersive device such as a diffraction grating can be utilized to tune to an absorption line associated with the gas of interest and a transmission line which is off of the absorption line associated with the gas of interest, an example of the use of this technology can be found in U.S. Pat. No. 3,939,348 which issued to J. J. Barrett on Feb. 17, 1976. In this patent, a Fabry-Perot Interferometer is used to provide a plurality of transmission windows regularly spaced in frequency. Selectively separated periodic spectra which are made up of a plurality of the rotational, vibrational infrared absorption lines associated with the gas of interest are transmitted in the form of a fringe thereby providing a detectable signal from which a determination of the amount of the particular gas of interest can be made. The Fabry-Perot Interferometer which is essential to the operation of this arrangement provides a mirror separation which can be adjusted to simultaneously transmit all of the rotational vibrational infrared absorption lines of a molecular species of the gas of interest. This approach to gas analysis or measurement has provided an advantage in that the sensitivity achieved has been an advance over the existing techniques. However, by relying on a mechanical arrangement for providing the selective separation of the periodic spectra, this approach suffers from certain limitations inherent in the use of a mechanical modulation arrangement. For instance, the accuracy and therefore the sensitivity of this approach is dependent upon the ability to accurately align the mirror elements of the Fabry-Perot Interferometer to the precise bandwidth desired. Additionally inherent in the operation of such mechanical arrangement is the limitation that modifying the operating characteristics of this measurement technique requires a cumbersome and time consuming manual operation involving the actual alignment or tuning of the mirror separation and the verification of the results of this alignment.

Similar to the limitations of the solid electrolyte cell and the AOTF device as applied to a situation requiring the quick, accurate detection or quantification of a gas of interest from a position distant from the environment under study, this use of the etalon device also requires the placement of such device based instrument in the specific area that is to be monitored. Accordingly, this approach also lacks the ability to be operated in a remote survey or scanning mode such that random, removed areas can be tested for the presence or quantity of the gas of interest.

SUMMARY OF THE INVENTION

It is therefore an object of the present invention to provide a method and apparatus for quickly and accurately determining the presence and/or quantity of a particular gas of interest from a remote position wherein the instrument incorporating such method and apparatus can be portably operated in a scanning mode to test random, undefined areas for such gas of interest.

With this object in mind, the present invention provides a method and apparatus for determining the presence and/or quantity of a gas of interest based on a measurement of the optical absorption line characteristics of the gas of interest. The gas measurement arrangement includes a source of electromagnetic radiation which projects light towards the area under test such that a back reflected light signal will be generated which possesses information determinative of gases in its path. A receiving arrangement receives the light signal and passes it along a light modulating arrangement which modulates the light signal to a first frequency representative of an intensity value of the light signal. Another modulating arrangement which modulates the light signal to a second frequency, includes a birefringent etalon device having associated therewith a periodic spacing equal to the periodicity of the absorption lines of the gas of interest. This modulating arrangement is further effective for applying an electric field such that the periodic transmission spectra are shifted between spectra which exactly coincide with the absorption lines and spectra which fall between the absorption line. A detecting arrangement can distinguish between the light signal at the first frequency and at the second frequency and as a result thereof, factor out the light intensity value such that the light signal is only representative of the quantity of the gas of interest.

BRIEF DESCRIPTION OF THE DRAWINGS

The preferred embodiment of the invention will be described by way of example, with reference to the accompanying drawings in which:

FIGS. 3A-G are graphical representations of the absorption spectra of a gas of interest and the correlation and anti-correlation spectra with various levels of finesse of the etalon.

DESCRIPTION AND OPERATION

Figure 1:
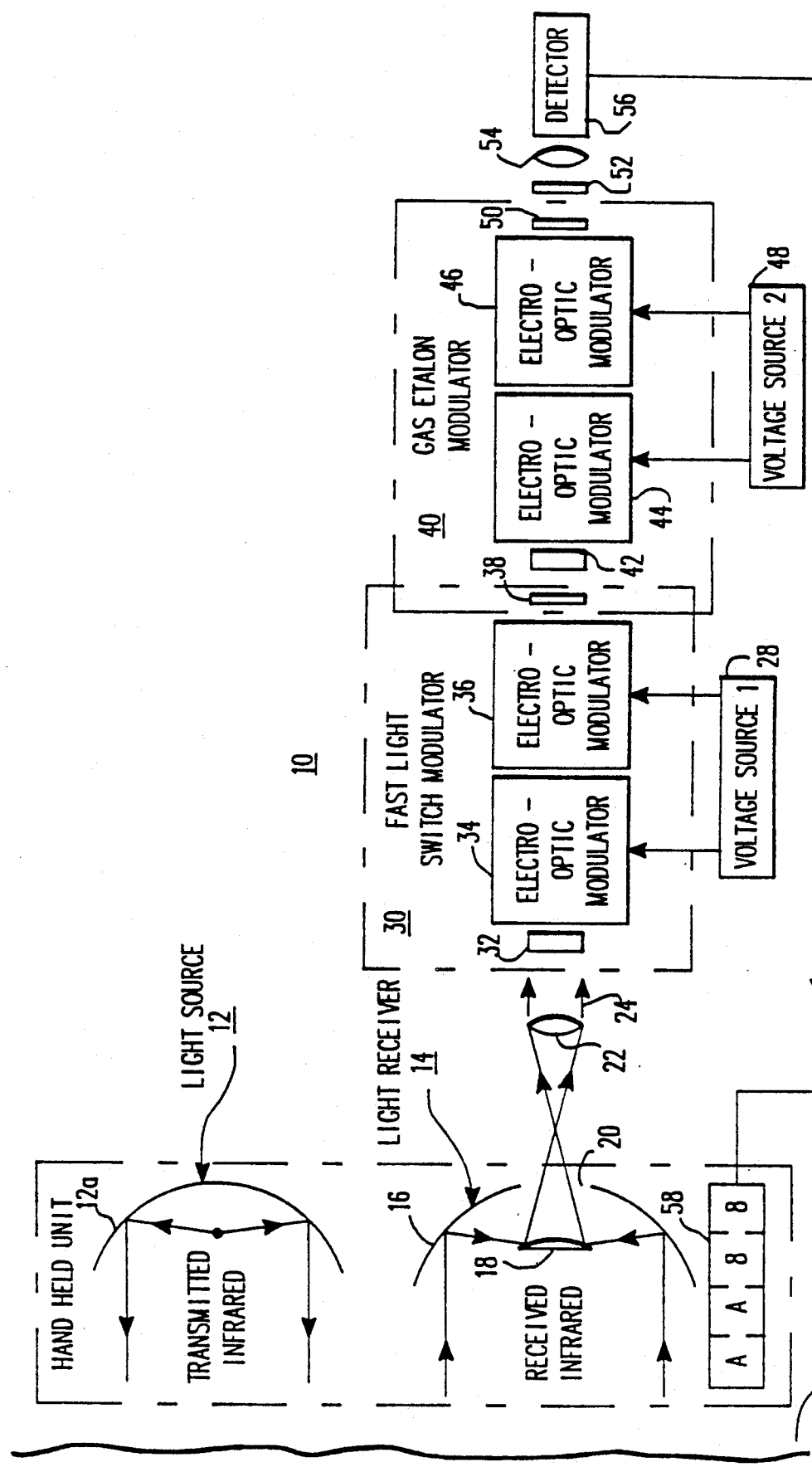
FIG. 1 is an elevational view partly in block diagram form of a gas measurement apparatus constructed in accordance with the present invention.

The present invention will be more readily understood following a general discussion of the field of differential absorption spectroscopy. In this field of differential absorption spectroscopy it is known to measure the absorption at a wavelength in the absorption band of the gas of interest and to compare this absorption to that which is measured at a reference wavelength, the reference wavelength being at a region where the gas of interest exhibits minimal if any absorption characteristics. It is further known that the ratio of these two absorptions produces a value that can be utilized in determining the concentration of the gas of interest. It can be appreciated that the practice of differential absorption spectroscopy is inherently more safe than the use of a non-dispersive absorption spectrometer which utilizes a reference sample cell of the gas of interest as a comparison of the absorption characteristics with the sample gas of interest. In this approach, when one is attempting to detect or quantify an amount of a harmful substance such as hydrogen fluoride (HF), hydrogen chloride acid (HCL) or methane ($CH_4$), one must have as a reference material, a sample of that harmful substance.

In the field of differential absorption spectroscopy, it is known that one can achieve the modulation necessary by use of a dispersive device such a diffraction grating or by means of selected narrow band optical filters. In the present invention, however, the necessary modulation is achieved by applying an electric field to an electro-optical modulator such that the transmission spectra is shifted half the distance between the maxima by applying what is referred to as a halfwave voltage to the modulator. Of course, it should be understood that the shifted transmission spectra need not fall precisely at the halfway point but is selected to fall at that point where the least absorption interference exists. In the past, birefringent etalon devices have been modulated by means of mechanical arrangements which require that in order to modify the specific absorption wavelength such that an alternate gas could be recognized, it was necessary to modify the spacing or other mechanical relationship to achieve the different absorption wavelength necessary. With this limitation there would be no flexibility in the use of that particular birefringent etalon for the detection or quantification of any gas of interest other than the particular one for which it was constructed. By separating the modulation function from the etalon function, it can be appreciated that different gases of interest can be detected and quantified by merely substituting an alternate birefringent etalon into the overall system instrument.

In applying this technology to a situation such as the measurement of methane in a mine environment, consideration must be given to the practical limitations caused by such an environment. Specifically, consideration must be given to the fact that methane can occur in pockets which vary infinitely in size and concentration. Additionally, because coal mining follows the contour of the coal seam, the dimensions of the mine area vary significantly as well. Accordingly, in order to achieve the remote survey or scanning operation required so as to avoid human exposure to this dangerous gas, it is necessary to accommodate changes in intensity of the light beam that is directed to the area under test, such changes in intensity occurring as a result of the undefined contour of the background against which the light beam is reflected.

Because of the variations in intensity of the light reflected back to the measurement instrument, it can be appreciated that a primary concern regarding the performance of this instrument is the synchronization of the specific light signal received back with the positioning or aiming that is done with the light source that is projected in the area under test. In other words, the operator of the instrument st be certain that the reading provided is the correct reading for the area that he has just surveyed or scanned. In order to assure that this is the actual case, the instrument must be capable of performing the projection, modulation and detection functions in as fast a manner as possible. For this reason, it is obvious that prior art interferometric arrangements which utilize mechanical modulation techniques are wholly inadequate for the present purpose. As seen in FIG. 1, a gas analyzer or measurement arrangement that would meet these conditions is shown generally as reference numeral 10. This gas analyzer arrangement 10 includes a light source 12 which is effective for generating the electromagnetic radiation that is to be directed toward the area suspected of containing the gas of interest. In this illustration, the light source 12 includes a quartz halogen spotlight having associated therewith, a parabolic reflector 12a which in conjunction, serve to emit infrared radiation in a directed manner. It should be understood that other sources of electromagnetic radiation are contemplated as being within the scope of the present invention; for instance, depending on the spectra at which the gas of interest exhibits the optimum detectable absorption characteristics, it may be necessary to use an ultraviolet light source instead of an infrared one.

The transmitted infrared from the light source 12 is directed toward the coal face or in fact, any other surface remote from the light source 12 between which the gas of interest can accumulate and for which the surface will provide the necessary back reflection of a portion of that electromagnetic radiation projected toward it. The back reflected electromagnetic radiation is picked up by a receiving arrangement 14 which is constructed in the form of a collection cassegrain. In this manner back reflected infrared radiation is reflected off of a parabolic surface 16 toward a focusing lens 18 and then through an opening 20. In addition to the use of a collection cassegrain, one skilled in the art would realize that the light receiving arrangement could be satisfied by the use of an alternate lens arrangement as for instance, a collecting telescope.

The back reflected light from the receiving arrangement 14 falls on a light conditioning arrangement 22 which in this case can be provided by a collimating lens or the like. The collimating lens 22 is effective for directing the back reflected light hereinafter referred to as light signal 24, into a parallel stream of light which can be efficiently directed along the optical path formed by the components of the gas analyzer arrangement 10 of the present invention.

It will be understood that light signal 24 will contain the necessary information from which the determination of the presence and/or quantity of the gas of interest as may occur in the path of the projected light source 12 may occur; that is, the light signal 24 will indicate whether and how much absorption has occurred in the specific spectra associated with the gas of interest. Light signal 24, after passing through the light conditioning arrangement 22, is optically coupled to a fast light switch modulator illustrated in the dotted line block designated 30 in FIG. 1.

The fast light switch modulator 30 consists essentially of an input polarizer 32 which is effective for polarizing the light signal 24 in a specific direction, followed by a pair of electro optical modulating devices 34 and 36 which are constructed of a material having a high electro-optical coefficient, and then followed by a second polarizer 38 which is oriented in the same polarization direction as the input polarizer 32.

Figure 2A:
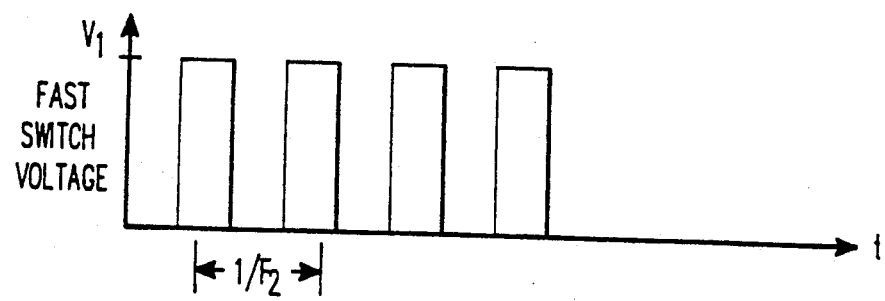
FIGS. 2A through C are graphical representations of the absorption spectra of the gas of interest as it relates to the light signal at the first and second frequencies.

As configured in the present manner, the components of the fast light switch modulator 30 achieve a phenomenon known as the "Pockels" effect; such effect has the characteristic that, with the input polarizer 32 and the second polarizer 38 oriented in a parallel direction in the absence of an electric field applied to the electro-optical modulators 34, 36, all of the light signal 24 that passes through the input polarizer 32 also passes through the second polarizer 38. Subsequently, when an electric field is applied to the electro-optical modulators 34, 36, the linearly polarized light from the input polarizer 32 is rotated, wherein the degree of rotation increases with the magnitude of the applied electric field. As it rotates, less and less of the light signal 24 is transmitted through the second polarizer 38 until, when a 90° rotation occurs, the light signal 24 is completely blocked from passage through the second polarizer 38. In one embodiment of the present invention, the fast light switch modulator 30 is driven at a frequency of 100 kHz which thereby results in a 100 kHz signal which is proportional to the intensity of the light signal 24. The light signal 24, modulated to this first frequency of 100 kHz is illustrated in FIG. 2A as a representative voltage $v_1$. For the purpose of providing the necessary electric field to the electro-optical modulator configuration 34, 36 of the fast light switch modulator 30, there is included as a component thereof, a first voltage source 28 which can be a conventional voltage source configured so as to provide the necessary voltage at the first frequency.

As the light signal 24 is completing its passage through the last element of the fast light switch modulator 30, this last element being the second polarizer 38, it has actually begun its passage through the next system component, the gas etalon modulator configuration illustrated in FIG. 1 in the dotted line block segment designated reference number 40. Because the second polarizer 38 operates in both the fast light switch modulator 30 as well as the gas etalon modulator 40 this element is common to both configurations.

The gas etalon modulator configuration 40 shown in FIG. 1 essentially serves the purpose of determining the amounts of the received light signal 24 that has been removed by the absorption characteristics of the gas of interest. The gas etalon modulator 40 includes the second polarizer 38 which is shared with the fast light switch modulator 30 as well as a birefringent etalon device 42. The birefringent etalon device 42 has associated therewith, a free spectral range which matches the gas of interest in one transmitted polarization and correlates with the gas absorption spectra, but whose transmitted spectrum anti-correlates with the gas of interest in the orthogonal polarization.

Etalon devices of the type used herein, can be constructed of a suitable birefringent material such as a crystalline quartz; other examples of materials suitable for construction of etalon devices are: potassium dihydrogen phosphate (KDP), potassium di-Deuterium phosphate (KD*P), and ammonium dihydrogen phosphate (ADP). Additionally, the material lithium niobate can be used in an application of an etalon device where the direction of propagation of the light beam is transverse to the application of the electrical field used to modulate the birefringent etalon device.

Disposed next within the gas etalon modulator 40 adjacent the birefringent etalon device 42 is a second electro-optical modulator configuration 44, 46 which, similar to the electro-optical modulator 34, 36 of the fast light switch modulator 30, is constructed of a material having a high electro-optical coefficient. It should be understood that the second electro-optical modulator 44, 46 can be constructed of a pair of modulator elements or can in fact, perform the necessary modulation function when provided in the form of a single electrooptic modulator device.

Figure 2B:
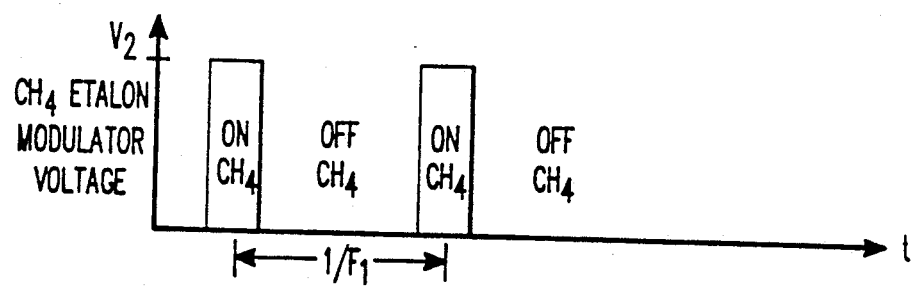

A second voltage source 48 is included as an element of the gas etalon modulator configuration 40 for the purpose of providing the necessary electric field to the second electro-optical modulator 44, 46. The second voltage source 48 provides a voltage $v_2$ at a second frequency $f_2$ which allows for the selection between the two periodic transmission spectra associated with the birefringent etalon device 42, these two spectra being the correlation and anti-correlation spectra. The relationship of the second voltage $v_2$ and the second frequency $f_2$ to the periodic spacing associated with the birefringent etalon 42 can best be seen with reference to the waveform of FIG. 2B wherein it can be seen that the voltage $v_2$ applied to the second electro-optical modulator 44, 46 is provided at a frequency $f_2$ which is one half ($\frac{1}{2}$) the frequency $f_1$ at which the voltage $v_1$ is provided to the electro-optical modulator 34, 36 of the fast light switch modulator 30. FIG. 2B further illustrates that for the anti-correlation spectra of the birefringent etalon 42, that is, the spectra at which the gas of interest exhibits no absorption properties, also occurs at one half ($\frac{1}{2}$) of the rate of the frequency $f_1$. For purposes of discussion, it should be noted that for frequency $f_2$ to be one half ($\frac{1}{2}$) of frequency $f_1$ previously stated to be 100 kHz, frequency $f_2$ must be set to 50 kHz. In this manner, the shifting between the correlation and anti-correlation spectra can occur at a fast enough rate to prevent errors from arising which may otherwise occur as a result of background movement during the cycle time of one absorption measurement. It should further be understood that the selection of these two frequencies was for illustration purposes only and that other frequencies above and below these values could also be used and still fall within the scope of the present invention. It should also be noted that the voltage sources 28, 48 illustrated herein are representational only and can in fact be substituted for by a single voltage source and a frequency dividing device.

A third polarizer element 50 is also included as a part of the gas etlon modulator 40 and is oriented in a manner so as to pass only selected spectra. The light signal 24 passes through the gas etalon modulator 40 to a filter device 52 and lens element 54 configuration which are effective for removing unwanted wave portions of the light signal 24, prior to being input to the detector configuration 56.

Figure 2C:
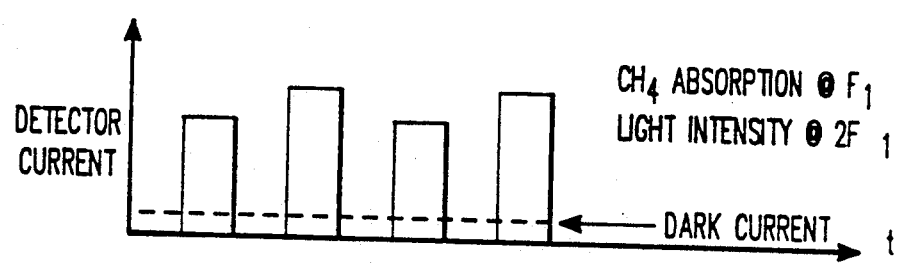

The detector configuration 56 determines the amount of the gas of interest present in the area under study by conventional means using the ratio of the absorptions between the correlation and anti-correlation spectra. Additionally, the detector configuration 56 performs the function of dividing the light signal at 50 kHz by the light signal 100 kHz which yields a signal that is proportional only to the gas concentration and is independent of the received light intensity value. The wave form shown in FIG. 2c illustrates the independence between the gas concentration and the received light intensity factors in the form of a detector current measurement $i_d$. The output of the detector device 56 can be coupled to a display arrangement 58 shown as an alphanumeric display segment and disposed within a hand held unit also containing the light source 12 and receiving arrangement 14.

Figure 4A:
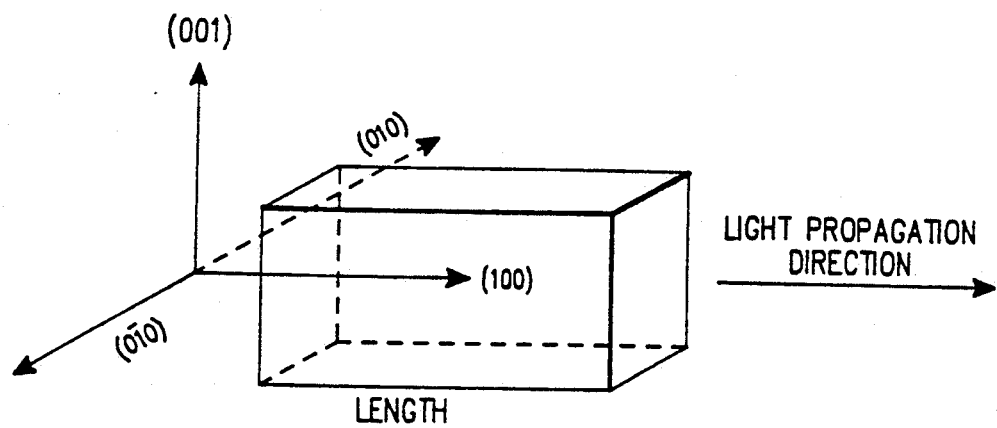
FIGS. 4A and 4B are elevational views in section of an etalon device constructed in accordance with an embodiment of the present invention.
Figure 4B:
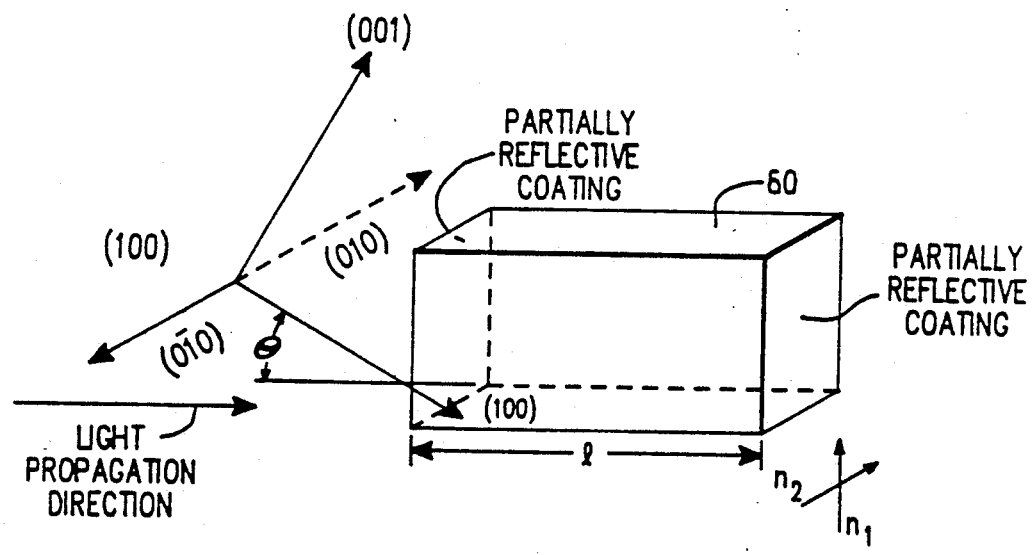
Figure 5:
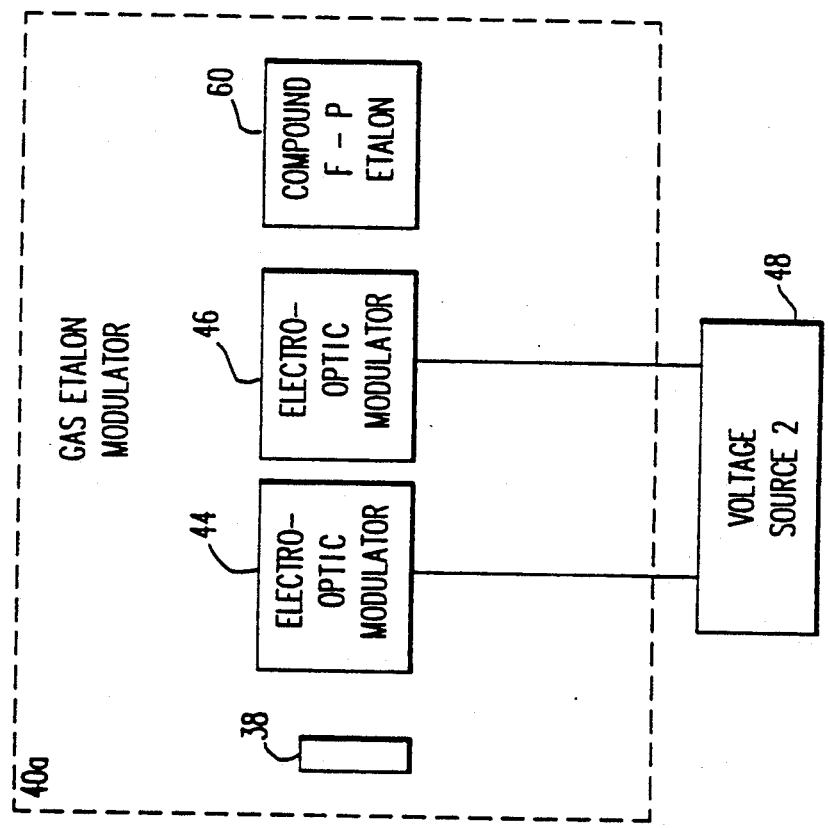
FIG. 5 is a block diagram representation of an alternate configuration of a gas etalon modulator.

As seen in FIG. 5, an alternate embodiment of the invention involves the substitution of the gas etalon modulator 40 shown in FIG. 1 with one utilizing a compound Fabry-Perot etalon constructed in the manner illustrated in FIGS. 4A and 4B. In this embodiment of the invention, it is desired to achieve a remote gas measuring arrangement which can be specifically applied to operate on a gas specie having associated therewith, a very precise narrow bandwidth absorption spectra. The technique of specifically tailoring a substantially identical registration of the absorption characteristics of certain gases, is commonly referred to as a high finesse or increased finesse technique. As seen in FIG. 3A, for gases which exhibit very precise absorption lines, if a filtering arrangement could be provided to substantially correlate with these lines, a more precise measurement essentially immune from interference would result. Accordingly, a gas analyzer arrangement which could provide for such precise correlation between the absorption spectra of the particular gas specie and the filtering capabilities of the interferometer arrangement should also provide a precise tailoring of the anticorrelation waveshape with which the absorption spectra is compared. It should be understood that having the capability to tailor the anti-correlation waveshape in a manner illustrated in FIG. 3G, will allow for a more accurate determination of the presence and/or quantity of the gas of interest due to the fact that interference from other gases which may have absorption lines in the region under observation, can be avoided. For instance, the anti-correlation lines need not be constructed so as to fall directly between the correlation lines but in fact, because of the ability to precisely specify the location of these lines, they can be disposed near the correlation lines so as to avoid any absorption lines of another gas which may interfere with the accuracy of this desired measurement.

Such a remote gas measuring arrangement can also be realized by the configuration illustrated in FIG. 5 wherein a compound Fabry-Perot etalon 60 is used in conjunction with the electro-optical modulator 44, 46 to achieve the high finesse gas analyzer arrangement. The compound Fabry-Perot etalon 60 is further shown in FIG. 4B wherein it is shown that the structure is such that the path length 1, in conjunction with the index of refraction $n_2$, creates the exact registration of the gas specie of interest.

To achieve the necessary indices of refraction that yield the specific correlation and anti-correlation waveshapes, the opposing surfaces formed along the longitudinal axis of the birefringent etalon 60 are coated with a partially reflective surface coating. The amount of reflectivity achieved by the surface coating is determinative of the sharpness of the absorption lines and hence, the high degree of finesse achieved as illustrated in FIG. 3G. Accordingly, it can be appreciated that by varying the amount of surface coating reflectivity, the finesse can be increased or decreased to achieve the sharpness necessary for the anti-correlation waveform to avoid absorbing interference of another gas specie.

The index of refraction $n_1$, is determinative of the spacing of the anti-correlation waveshape and can be specified so as to achieve this spacing relative to the correlation waveshape as is necessary to avoid such interference from the absorption spectra of other gas species. The manner by which the selective spacing of the anti-correlation waveform can be achieved is best illustrated in FIG. 4B wherein the optical axii of the compound Fabry-Perot interferometer 60 are illustrated. As illustrated, the index of refraction $n_2$ which is determinative of the correlation waveform frequency spacing, is disposed along the (010) axis and, since this frequency spacing must correlate with the absorption spectra of the gas of interest, this index of refraction $n_2$ must be set and not be variable. The index of refraction $n_1$ however is variable without affecting the disposition of $n_2$ and can be seen to vary from $\theta=0°$ to $\theta=90°$ wherein, should $\theta=90°$, $n_1=n_2$ and where $\theta=0°$, $n_1=n_2$ with $n_z$ being the index of refraction when the optical axis (001) is disposed relative to the axii (100) and (010) as is illustrated in FIG. 4A; that is, when the optical z axis is disposed orthogonal to the plane formed by the optical x and y axii. This selection effectively moves the anti-correlation lines shown in FIG. 3G between the correlation lines to the optimum position to prevent interference and to thereafter set, for the remaining operating life cycle of the gas analyzer arrangement, those indices of refraction once the material structure has been cut.

In operation, the gas analyzer arrangement 10 can be remotely operated as a hand held instrument whereby the instrument operator points the light source 12 in the area of concern such that the electromagnetic radiation is directed through a suspected quantity of the gas of interest and thereafter back reflected to the receiving arrangement 14 which can also be contained within the hand held portion of the gas analyzer arrangement 10. The back reflected light signal is picked up by the parabolic portion 16 of the receiving arrangement 14 and directed through the opening 20 by means of lens 18. The light signal from the receiving arangement 14 then passes through the collimating lens 22 which directs the light beam in the parallel stream identified as light signal 24 and which has associated therewith, absorption spectra indicative of the presence of those gases, through which the electromagnetic radiation has passed. Although light signal 24 may contain absorbed spectra indicative of numerous gases, for the present purpose, this operation will be described with reference to a particular gas such as methane which has an absorption band near 3.4 micrometers in the infrared region. In the presence of methane the infrared radiation in this region will be reduced relative to the radiation in adjacent regions where no methane absorption exists, if the gas concentration in the measurement path world be sufficiently high.

From the collimating lens 22, the parallel focused light signal 24 is then optically coupled to the fast light switch modulator 30. The input polarizer 32 of the fast light switch modulator 30 passes that portion of the light signal 24 which coincides with the direction of polarization which polarizer 32 is oriented. The polarized light signal 24 then passes through the electrooptical modulator configuration 34, 36 which configuration has applied thereto, a first voltage $v_1$ modulated to a first frequency $f_1$ and which in this instance, is set at 100 kHz.

As the light signal 24 passes through the electro-optical modulator configuration 34, 36, the applied electric field has the effect that, for each cycle associated with the electric field, the fast light switch modulator 30 acts as a filter such that one half of the filtered light signal 24 is blocked from exiting the fast light switch modulator 30. This filtering affect is achieved by the fact that the electric field shifts the polarization of the light signal 24 by 90° so that it cannot pass through the second polarizer 38 which is oriented in a parallel direction to that of the input polarizer 32. This Pockels effect phenomenon is illustrated by the waveform of FIG. 2A where it can be seen that, when the electric field is at voltage $v_1$ for one half of the frequency $f_1$, the orientation of the light signal 24 will be shifted so as to not pass through the second polarizer 38. Accordingly, the light signal 24 will resemble the waveform in FIG. 2A in terms of its period.

The light signal 24 at the first frequency $f_1$ is optically coupled to the gas etalon modulator configuration 40 by means of the sharing arrangement of the second polarizer 38 with the fast light switch modulator 30. Light signal 24 is then passed to the birefringent etalon device 42 which has been sized specifically to correlate to the known absorption spectra of the gas of interest. For purposes of discussing the operation of the birefringent etalon device 42, reference will be made to the waveforms of FIGS. 3A through C. Where FIG. 3A illustrates the absorption spectra of the gas of interest, FIG. 3B illustrates the correlation waveform associated with the birefringent etalon device 42 and FIG. 3C illustrates the anti-correlation waveform associated with the etalon device 42.

With the light signal 24 passing through the birefringent etalon device 42 during the correlation phase, all of the radiation that passes through the etalon device 42 is capable of being strongly absorbed by the gas of interest. During the anti-correlation condition, however, which occurs when the electric field is applied to the electro-optic modulator arrangement 44, 46, the light signal 24 has none of its radiation absorbed by the gas of interest. The presence of the gas therefore produces a very strong change in the relative intensities of the signals reaching the detector 56 during correlation and anti-correlation. It should be noted that the wavelength shift employed between the correlation and anti-correlation conditions can be as little as a 1/10 of a wave number or less, so that the same spectral range is observed for both parts of the differential measurement. Only a substance exhibiting the sharp spectral absorption lines and regular periodic spacing of the gas to be measured will produce such an absorption signal.

It should be further noted that the light signal 24 which has been previously modulated to a 100 kHz frequency by the fast light switch modulator configuration 30, is also modulated by the gas etalon modulator configuration 40 to a frequency of 50 kHz which is utilized by the gas etalon modulator arrangement 40 for purposes of shifting between the correlation and anticorrelation conditions.

By synchronizing commencement of the periods of the electric fields supplied by the first and second voltage sources 28 and 48, the effect of such double modulation scheme is that the gas etalon modulator configuration 40 will be in the anti-correlation condition for every other occurrence of the application of the voltage $v_1$ to the light signal 24.

The light signal 24, following shifting between the correlation and anti-correlation conditions, is directed through the third polarizer 50 and then through the filter 52 and lens configuration 54 where the light signal 24 is stripped of unwanted wave portions prior to being input to the detector arrangement 56.

The detector arrangement 56, before determining the concentration of the gas of interest that may be present in the area under test, must first distinguish between that portion of the received input light signal 24 which is representative of the intensity of the back reflected electromagnetic radiation and the portion of such light signal 24 as is representative of such gas concentration. For this purpose, the detector arrangement 56 divides the light signal 24 at the 50 kHz frequency by the light signal at the 100 kHz frequency which results in the generation of a signal representative only of the gas concentration; the portion of the light signal 24 representative of the intensity being effectively removed from consideration thereby.

The detector arrangement 56 utilizes conventional means to determine the presence and/or quantity of the gas of interest by the ratio of the intensity of the absorption lines at the transmission spectra maxima and the point selected between the transmission spectra maxima for the anti-correlation waveform.

Although the above discussion describes the preferred embodiment of the invention, it can be appreciated that modifications can be made thereto without departing from the scope of the present invention as set forth in the appended claims.

We claim:

1. An apparatus for rapid scanning of the concentration of a remote gas of interest using optical absorption line characteristics of such gas, said measuring apparatus comprising:

a broadband source of infrared radiation;

means for direction the broadband infrared radiation to a remote, reflection surface;

means for receiving a reflected portion of the infrared radiation, wherein the intensity of the reflected portion is subject to unpredictable change due to shifts in infrared radiation transmission direction crossing areas of varying concentration of the gas of interest and hitting reflective surfaces of differing albedo;

light modulator means optically coupled to said receiving means for modulating said reflected portion at a first frequency and outputting a modulated reflected portion;

means for modulating said modulated reflected portion at a second frequency related to the first frequency by an integral factor, said modulating means including a birefringent etalon device having a periodic spacing equal to the periodicity of the absorption lines of the gas of interest, said modulating mean further effective such that, with an electric filed applied thereto, the periodic transmission spectra of said birefringent etalon device is shifted between spectra which coincide with such absorption line characteristics and spectra which fall between such absorption line characteristics, and outputting a twice modulated reflected portion; and means for distinguishing between said twice modulated reflected portion at such first frequency and at such second frequency and determining therefrom, at least a quantity of such gas of interest.

2. A remote gas measuring apparatus as set forth in claim 1 wherein said source of infrared radiation and said receiving means are contained within a hand held unit which can be manually operated such that infrared radiation can be projected in a scanning manner.

3. A remote gas measuring apparatus as set forth in claim 2 wherein said hand held unit is directed toward such area having a background surface against which such infrared radiation can be back reflected toward said receiving means.

4. A remote gas measuring apparatus as set forth in claim 1 wherein said light modulator means includes an input polarizer element and a second polarizer element which is oriented in the same direction of polarization as the input polarizer element.

5. A remote gas measuring apparatus as set forth in claim 4 wherein said light modulator means further includes an electro-optical modulator arrangement disposed between said input polarizer and said second polarizer elements and effective, upon the application of an electric field having associated therewith said first frequency, such that the polarization of said light signal is rotated to a different polarization which said second polarizer element blocks from passage therethrough.

6. A remote gas measuring apparatus as set forth in claim 1 wherein said means for modulating includes as an input element thereof, a polarizer element, said modulator means further including a second electrooptical modulator configuration disposed following said birefringent etalon device such that, after said light signal has passed through said birefringent etalon device, said light signal can be modulated to a second frequency whereby upon such modulation, such shifting in the periodic transmission spectra between spectra which coincide with such absorption lines and spectra which fall between such absorption lines can be achieved.

7. A remote gas measuring apparatus as set forth in claim 1 wherein said distinguishing means, in determining such quantity of such gas of interest, first divides said light signal at said second frequency by said light signal at said first frequency thereby factoring out, an intensity value associated with said light signal at said first frequency.

8. A remote gas measuring apparatus as set forth in claim 7 wherein said distinguishing means further determine such quantity of such gas of interest by comparing such spectra which coincides with such absorption lines and such spectra which fall between such absorption lines.

9. A method of remotely measuring a gas of interest by its optical absorption line characteristics, said remote measuring method comprising the steps of:

directing a light beam to an area backed by a reflective surface, where such gas of interest may be such that a light signal representative of such absorption line characteristics can be back reflected toward a light signal receiving device;

collecting such back reflected light signal by such receiving device;

passing said light signal through a light modulating arrangement such that such light signal is modulated at a first frequency;

directing said light signal modulated at said first frequency through a birefringent etalon device which has associated therewith, a periodic spacing substantially equivalent to such absorption lines associated with such gas of interest;

applying an electric field to a modulating arrangement associated with such birefringent etalon to modulate such once modulated light signal between spectra which substantially coincide with such absorption lines and spectra which fall between such absorption lines, said electric field having associated therewith a second frequency distinct from such first frequency and related thereto by a whole integer factor other than one; and distinguishing between such light signal at such first frequency and such light signal at such second frequency an determining therefrom at least a quantity of such gas of interest.

10. A remote gas measuring method as set forth in claim 9 further comprising the steps of polarizing such light beam prior to said passing of said light beam to such light modulator arrangement and conditioning such light signal after said step of directing said light signal through such birefringent etalon device such that certain known portions of such light signal are removed prior to said distinguishing step.

11. An apparatus for remotely measuring a gas of interest by is optical absorption line characteristics, said remote measuring apparatus comprising:

a source of electromagnetic radiation;

means for directing such electromagnetic radiation through such as of interest to a remote, reflective surface;

mans for receiving a reflected light signal produced as a result of such electromagnetic radiation passing through such gas of interest and having at least a portion thereof reflected in a direction toward said receiving means;

light modulator means optically coupled to said receiving mean for once modulating said light signal at a first frequency;

means for modulating said once modulated light signal at a second frequency related to said first frequency by a whole integer factor other than one, said modulating means including an interferometric device receptive of said light signal and having associated therewith, a periodic spacing equal to the periodicity of the absorption lines of such gas of interest, said interferometric device further having associated therewith, a second periodic spacing substantially equivalent to transmission spectra which fall between such absorption lines, to produce a twice modulated light signal;

wherein said interferometric device is modulated between said first and said second frequency be application of an electric field thereto, and means for detecting at least an amount of such gas of interest as a function of the intensity of such periodic transmission spectra.

12. A measurement arrangement as set forth in claim 11 wherein said interferometric device is a compound Fabry-Perot birefringent etalon device having associated therewith, a first index of refraction and a path length which determine, in conjunction, such periodic transmission spectra which substantially coincides with such absorption lines associated with such gas of interest.

13. A measurement arrangement as set forth in claim 12 wherein said birefringent etalon device further has associated therewith, a second index of refraction which determines such periodic transmission spectra which falls between such absorption lines associated with said gas of interest.

14. A measurement arrangement as set forth in claim 13 wherein said second index of refraction can be selected from a range of values such that such periodic transmission spectra which falls between such absorption lines associated with the gas of interest, occur at a wavelength which essentially avoids interference from gases other than such gas of interest.

15. An apparatus for rapid scanning of the concentration of a remote gas using optical absorption line characteristics of the gas, the apparatus comprising:

a source of electromagnetic radiation;

means for directing the electromagnetic radiation toward a remote, reflective surface;

means for receiving reflected electromagnetic radiation from the remote surface;

a light switch optically coupled to said receiving means for producing polarized pulses of light at a first frequency from the reflected electromagnetic radiation;

a birefringent etalon optically coupled to the light switch, the etalon having periodic transmission spectra shiftable between first spectra which coincide with such absorption lien characteristics and second spectra which fall between such absorption line characteristics, to produce pulses containing the first spectra and pulses containing the second spectra;

means for distinguishing the pulses containing the first spectra and the pulses containing the second spectra;

means for correlating pulses of the first spectra and pulses of the second spectra in time;

means for determining gas concentration from correlated pulses of the first spectra and the second spectra.

* * * * *

UNITED STATES PATENT AND TRADEMARK OFFICE
CERTIFICATE OF CORRECTION

PATENT NO. : 5,076,699
DATED : December 31, 1991
INVENTOR(S) : FREDERICK M. RYAN, MILTON S. GOTTLIEB It is certified that error appears in the above-identified patent and that said Letters Patent is hereby corrected as shown below:

Col. 5, line 13, delete "st", insert "must"

Col. 7, line 62, delete "etlon", insert "etalon"

Col. 9, line 64, delete "world", insert "would"

Col. 11, line 45, delete "direction", insert "directing"

Col. 11, line 46, delete "reflection", insert "reflecting"

Col. 13, line 20, delete "an", insert "and"

Col. 13, line 35, delete "as", insert "gas"

Col. 14, line 43, delete "lien", insert "line"

Signed and Sealed this

Twenty-sixth Day of October, 1993

Attest:

BRUCE LEHMAN

*Attesting Officer*   *Commissioner of Patents and Trademarks*